(12) United States Patent
Pero et al.

(10) Patent No.: US 6,538,038 B1
(45) Date of Patent: Mar. 25, 2003

(54) COMPOSITIONS AND METHODS FOR USE IN TARGETING VASCULAR DESTRUCTION

(75) Inventors: Ronald W. Pero, Lund (SE); David Sherris, Jamaica Plain, MA (US)

(73) Assignee: OXiGENE, Inc., Watertown, MA (US)

( * ) Notice: Subject to any disclaimer, the term of this patent is extended or adjusted under 35 U.S.C. 154(b) by 0 days.

(21) Appl. No.: 09/505,402

(22) Filed: Feb. 16, 2000

Related U.S. Application Data

(60) Provisional application No. 60/120,478, filed on Feb. 18, 1999.

(51) Int. Cl.⁷ .............................................. A61K 31/05
(52) U.S. Cl. ........................ 514/731; 424/600; 424/602; 424/603; 424/604; 424/605; 424/606; 514/733
(58) Field of Search ................................ 514/731, 733; 424/601–606

(56) References Cited

U.S. PATENT DOCUMENTS 5,529,989 A * 6/1996 Pettit et al. .................... 514/81

OTHER PUBLICATIONS

G.G. Dark et al., "Combretastatin A–4, an Agent That Displays Potent and Selective Toxicity Toward Tumor Vasculature," Cancer Research 57:1829–34 (1997).

International Preliminary Examination Report, PCT/US00/03996 (Report Dated Mar. 20, 2001).

* cited by examiner

Primary Examiner—Dwayne C. Jones
(74) Attorney, Agent, or Firm—Barry J. Marenberg; Ivor R. Elrifi; Mintz, Levin, Cohn, Ferris, Glovsky and Popeo, P.C.

(57) ABSTRACT

Treatment of warm-blooded animals having a tumor or non-malignant hypervascularation, by administering a sufficient amount of a cytotoxic agent formulated into a phosphate prodrug form having substrate specificity for microvessel phosphatases, so that microvessels are destroyed preferentially over other normal tissues, because the less cytotoxic prodrug form is converted to the highly cytotoxic dephosphorylated form.

12 Claims, 6 Drawing Sheets

CYTOTOXIC FORM

IX 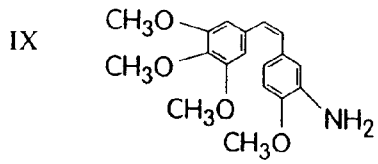

AMINO COMBRETASTATIN A4
1-(3 AMINO -4- METHOXY PHENYL)
2-(3,4,5 - TRI METHOXY PHENYL) - ETHENE

NON-CYTOTOXIC FORM

X 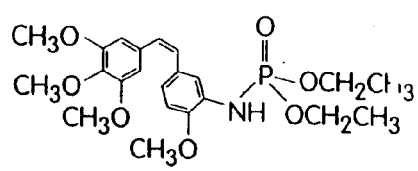

PM-VI-19C
AMINO COMBRETASTATIN A4
PHOSPHORO AMIDATE PRODRU

XI 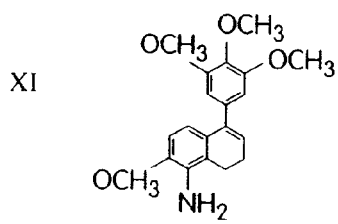

AMINO DIHYDRONAPHTALENE
ANALOG

XII 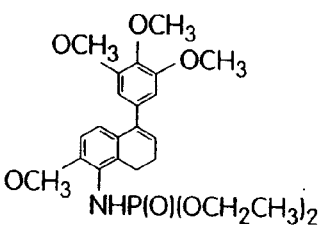

AMINO DIHYDRONAPHTALENE
PHOSPHORO AMIDATE

XIII 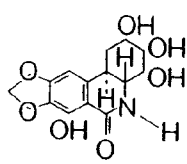

PANCRATISTATIN

XIV 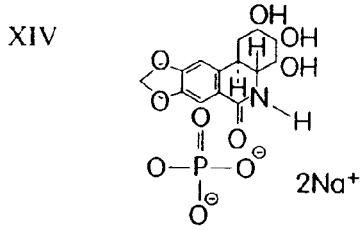

PANCRATISTATIN SODIUM
PHOSPHATE PRODRUG

XV 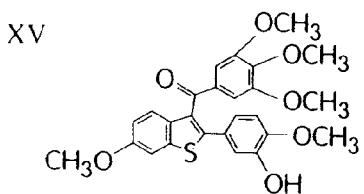

VPM-V-150
3-(3',4',5' -TRIMETHOXYBENZOYL) -2
(4'- METHOXY - 5' HYDROXY PHENYL) - 6 -
METHOXYBENZO (b) THIOPHENE

XVI 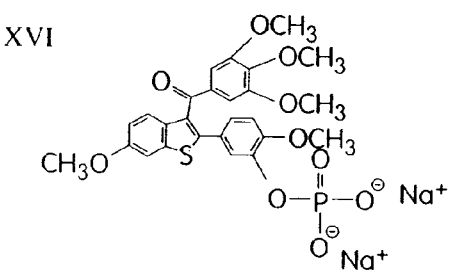

VPVM-V-152
BENZO(b)THIOPHENE SODIUM
PHOSPHATE PRODRUG

Fig. 1B

| CYTOTOXIC FORM | NON-CYTOTOXIC FORM |
|---|---|
| XVII  3-(3',4',5' TRIMETHOXY BENZOYL)-2-(4'-METHOXY 5'-HYDROXY PHENYL)-6-METHOXY INDOLE | XVIII  INDOLE SODIUM PHOSPHATE PRODRUG |
| XIX  COLCHICEINE | XX  COLCHICEINE SODIUM PHOSPHATE PRODRUG |
| XXI  2-METHOXYESTRADIOL | XXII  2-METHOXYESTRADIOL SODIUM PHOSPHATE PRODRUG |

US 6,538,038 B1

COMPOSITIONS AND METHODS FOR USE IN TARGETING VASCULAR DESTRUCTION

CROSS REFERENCE TO RELATED APPLICATION

This application claims the priority benefit of copending U.S. provisional patent application Ser. No. 60/120,478, filed Feb. 18, 1999.

BACKGROUND OF THE INVENTION

This invention relates to methods of and compositions for effecting targeted vascular destruction in warm-blooded animals, including humans, and to procedures for identifying drugs capable of such use.

The importance of vasculature to the growth of tumors is an unquestioned scientific reality. Because one blood vessel nourishes thousands of tumor cells, targeting tumor vasculature as a molecular approach to cancer chemotherapies is becoming one of the highest scientific priorities. Two drug models are emerging, i.e., one that prevents the formation of new blood vessels in the tumor (antiangiogenesis) and one that targets vascular destruction as a means of limiting tumor nourishment and/or the impermeability of the luminal surface of vessel endothelial cells to cancer drugs such as immunotherapies (New England Journal of Medicine 339:473–474, 1998). The antiangiogenic model is basically a cytostatic approach where angiogenic factors generally produced by tumors such as vascular endothelial growth factor (VEGF) and platelet derived endothelial cell growth factor, are blocked by antiangiogenic compounds such as the natural polypeptides angiostatin and endostatin to prevent new blood vessel growth (The Cancer Journal Scientific American 4(4):209–216, 1998; Cell 88:277–285, 1997). On the other hand, the vascular destruction model is a cytotoxic approach where tumor vessels are targeted for cytotoxicity in order to enhance tumor cell cytotoxicity by hypoxia or direct acting chemotherapy.

One of the most potent classes of cancer therapeutic drugs is the antimitotic tubulin polymerization inhibitors (Biochem. Molecular Biology Int. 25(6):1153–1159, 1995; Br. Journal Cancer 71(4):705–711, 1995; Journal Med. Chem. 34(8):2579–2588, 1991; Biochemistry 28(17):6904–6991, 1989). They characteristically have $IC_{50}$ in vitro cell cytotoxicities in the nM–$\mu$M range, but often show poor specificity for killing tumor over normal tissues in vivo, examples of such drugs including combretastatins, taxol (and other taxanes), vinblastine (and other vinca alkaloids), colchicinoids, dolastatins, podophyllotoxins, steganacins, amphethiniles, flavanoids, rhizoxins, curacins A, epothilones A and B, welwistatins, phenstatins, 2-strylquinazolin-4(3H)-ones, stilbenes, 2-aryl-1,8-naphthyridin-4(1H)-ones, 5,6-dihydroindolo (2,1-a) isoquinolines, 2,3-benzo(b)thiophenes, 2,3-substituted benzo(b)furans and 2,3-substituted indoles (Journal of Med. Chem. 41(16):3022–3032, 1998; Journal Med. Chem. 34(8):2579–2588, 1991; Anticancer Drugs 4(1):19–25, 1993; Pharm. Res. 8(6):776–781, 1991; Experimentia 45(2):209–211, 1989; Med. Res. Rev. 16:2067, 1996; Tetrahedron Lett. 34:1035, 1993; Mol. Pharmacol. 49:288, 1996; J. Med. Chem. 41:1688–1695, 1998; J. Med. Chem. 33:1721, 1990; J. Med. Chem. 34:2579, 1991; J. Md. Chem. 40:3049, 1997; J. Med. Chem. 40:3525, 1997; Bioorg. Med. Chem. Lett. 9:1081–1086, 1999; International (PCT) Application No. US 98/04380; U.S. Provisional Patent Application No. 60/154,639). Although tubulin binding agents in general can mediate effects on tumor blood flow, doses that are effective are often also toxic to other normal tissues and not particularly toxic to tumors (Br. J. Cancer 74(Suppl. 27):586–88, 1996).

Many tubulin binding agents such as the combretastatins and taxol analogs are water insoluble and require formulation before evaluation in the clinic. One approach which has been used successfully to overcome this clinical development problem is the formulation of biolabile water soluble prodrugs, such as the phosphate salt derivatives of combretastatin A4 and taxol, that allow metabolic conversion back into the water insoluble form (Anticancer Drug Des. 13(3):183–191, 1998; U.S. Pat. No. 5,561,122; Bioorganic Med. Chem. Lett. 3:1766, 1993; Bioorganic Med. Chem. Lett. 3:1357, 1993). A prodrug is a precursor which will undergo metabolic activation in vivo to the active drug. Stated with further reference to the aforementioned phosphate salt derivatives, the concept here is that non-specific phosphatases such as alkaline phosphatases in mammals are capable of dephosphorylating phosphate prodrugs into the original biologically active forms. This prior art teaches how to administer a water insoluble drug to warm blooded animals for therapeutic purposes under conditions of more maximum absorption and bioavailability by formulation into a water soluble biolabile form (Krogsgaard-Larsen, P. and Bundegaard, H., eds., A textbook of Drug Design and Drug Development, Harvard Academic Publishers, p. 148, 1991).

When the combretastatin A4 phosphate prodrug was used in in vitro and in vivo cell and animal models, it displayed a remarkable specificity for vascular toxicity (Int. J. Radiat. Oncol. Biol. Phys. 42(4):895–903, 1998; Cancer Res. 57(10): 1829–1834, 1997). It was not obvious from this to one skilled in the art that phosphate prodrugs in general, which serve as substrates for alkaline phosphatase, had anything to do whatsoever with vascular targeting. However, the reported data on the combretastatin A4 phosphate prodrug did disclose the principle of preferential vascular toxicity, even though there was no understanding or appreciation of the fact that the prodrug itself was responsible for vascular targeting. In other words, the prior art teaches that A4 and not A4 prodrug was responsible for vascular toxicity by assuming that there was no difference in vascular toxicity between the two forms. The nonobviousness noted above is exemplified by the fact that, although A4 phosphate prodrug and other taxol phosphate prodrugs were promoted as susceptible to phosphatase conversion to the cytotoxic tubulin binding forms, it was never recognized that this enzyme was elevated in microvessels thus targeting them to cytotoxicity.

SUMMARY OF THE INVENTION

An object of the invention is to provide compositions and methods useful in targeting the microvessel destruction model for the treatment, in warm-blooded animals including (but not limited to) humans, of cancer, Kaposi's sarcoma, and other, non-malignant vascular proliferative disorders such as macular degeneration, psoriasis and restenosis, and, in general, inflammatory diseases characterized by vascular proliferation.

Another object is to provide procedures for identifying drugs that are capable of use in producing such compositions and performing such methods.

To these and other ends, the present invention in a first aspect broadly contemplates the provision of a method of treating a warm-blooded animal having a vascular proliferative disorder, comprising administering, to the animal, an amount of a prodrug other than combretastatin A4 disodium phosphate effective to achieve targeted vascular destruction at a locality of proliferating vasculature, wherein the prodrug is substantially noncytotoxic but is convertible to a substantially cytotoxic drug by action of an endothelial enzyme selectively induced at enhanced levels at sites of vascular proliferation.

In a second aspect, the invention contemplates the provision of a method of treating a warm-blooded animal having a nonmalignant vascular proliferative disorder, comprising administering, to the animal, an amount of a prodrug effective to achieve targeted vascular destruction at a locality of proliferating vasculature, wherein the prodrug is substantially noncytotoxic but is convertible to a substantially cytotoxic drug by action of an endothelial enzyme selectively induced at enhanced levels at sites of vascular proliferation.

In a further aspect, the invention contemplates the provision of compositions for treating a warm-blooded animal having a vascular proliferative disorder to achieve targeted vascular destruction at a locality of proliferating vasculature, comprising a prodrug, other than combretastatin A4, pancratistatin and taxol phosphate prodrugs, which is substantially noncytotoxic but is convertible to a substantially cytotoxic drug by action of an endothelial enzyme selectively induced at enhanced levels at sites of vascular proliferation.

In yet another aspect, the invention provides a procedure for identifying prodrugs suitable for use in the above methods and compositions, such procedure comprising the steps of culturing proliferating endothelial cells, and other cells, in the presence of a prodrug other than combretastatin A4 disodium phosphate for a limited time period; comparing the respective cultures thereafter to determine whether the culture of proliferating endothelial cells exhibits a significantly greater cytotoxic effect than the culture of other cells; and, if so, culturing the aforesaid other cells in the presence of the prodrug and an endothelial enzyme selectively induced at enhanced levels at sites of vascular proliferation, enhanced cytotoxic effect with respect to the other cells in the presence of the enzyme as compared to the cytotoxic effect in the initial culture of the other cells indicating suitability of the prodrug for such methods and compositions. Conveniently or preferably, the "other cells" may be nonmalignant fibroblasts, e.g., normal human fibroblasts.

In an important specific sense, to which however the invention is in its broadest aspects not limited, the prodrug in the foregoing methods, compositions and procedures may be a phosphate within the class of compounds having the general formula

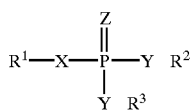

wherein
X is O, NH, or S;
Y is O, NH, S, $O^{31}$, $NH^-$ or $S^-$;
Z is O or S;
each of $R^2$ and $R^3$ is an alkyl group, H, a mono- or divalent cationic salt, or an ammonium cationic salt, and $R^2$ and $R^3$ may be the same or different; and
$R^1$ is defined by the formula $R^1$—$R^a$ representing a compound that contains at least one group (designated $R^a$) which is a group, containing X, that can form a phosphate or other salt that serves as a substrate for non-specific vascular endothelial phosphatases, and is thereby converted from a relatively non-cytotoxic phosphate form to a cytotoxic $R^1$—$R^a$ form.

Currently preferred prodrugs for the practice of the invention are those having the following formulas:

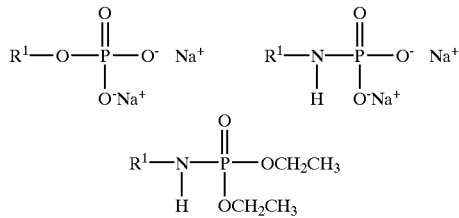

More particularly, the compound with formula $R^1$—$R^a$ may be a tubulin binder. In specific aspects it may be selected from the known tubulin binding agents already previously listed such as the combretastatins, taxanes, vinblastine (vinca alkaloids), colchicinoids, dolastatins, podophyllotoxins, steganacins, amphethiniles, flavanoids, rhizoxins, curacins A, epothilones A and B, welwistatins, phenstatins, 2-strylquinazolin-4(3H)-ones, stilbenes, 2-aryl-1,8-naphthyridin-4(1H)-ones, 5,6-dihydroindolo(2,1-a)isoquinolines, 2,3-benzo(b)thiophenes, 2,3-substituted benzo(b)furans and 2,3-substituted indoles. In a still more specific sense, this tubulin binder may be a compound selected from the group consisting of combretastatins (other than combretastatin A4), colchicine, and 2-methoxy estradiol.

Stated with reference to phosphate prodrugs, for an understanding of the invention it may be explained that vascular endothelial cells have high levels of phosphatase activity because of (i) stress injury response of microvessels due to blood circulation (J. Invest. Dermatol. 109(4):597–603, 1997) and (ii) the induction of phosphatase in vascular endothelial cells by IL-6 produced by inflammatory cells during wound healing or by invasive tumor cells (FEBS Lett. 350(1):99–103, 1994; Ann. Surg. Oncol. 5(3):279–286, 1998). High levels of phosphatases (e.g. alkaline) are a part of the normal physiology of microvessels, because together with the blood clotting mechanism, calcium deposits generated from alkaline phosphatase activity aid in the wound healing process. The present invention embraces the discovery that phosphate or other appropriate prodrug constructs, which become substrates for phosphatases such as alkaline phosphatases, are useful in targeting microvascular toxicity. Examples of phosphatase enzymes suitable for this purpose require an ectoplasmic cellular location because of the poor absorption of phosphorylated molecules through the cytoplasmic membrane. Dephosphorylating enzymes known to have an ectoplasmic location are non-specific alkaline phosphatases, ATPase, ADPase, 5'-nucleotidase, and purine nucleoside phosphorylase. Another property necessary for targeting cytotoxic agents by dephosphorylation via phosphatases is that they could utilize a broad spectrum of phosphate prodrugs as substrates. In this regard, alkaline phosphatase is an attractive target for delivering selective toxicity to vascular endothelial cells.

Further features and advantages of the invention will be apparent from the detailed description hereinbelow set forth, together with the accompanying drawings.

BRIEF DESCRIPTION OF THE DRAWINGS

FIGS. 1A, 1B and 1C illustrate the structures of various cytotoxic compounds and noncytotoxic prodrugs thereof as examples of molecular diversity capable of targeting microvascular cellular toxicity by formation of phosphate prodrugs;

FIGS. 3A and 3B are graphs showing the effect of alkaline phosphatase on cultured HMVEC and HDF;

FIGS. 4A and 4B are graphs showing the dose response effect of added alkaline phosphatase on the cytotoxicity of HMVEC and HDF to A4 prodrug; and FIG. 5 is a series of graphs showing the effects of exposure time on the clonogenic toxicity induced by a variety of tubulin binding drugs.

DETAILED DESCRIPTION

This invention embraces the use of phosphate prodrugs comprising administering to warm-blooded animals having a tumor or non-malignant hypervascularation, a sufficient amount of a cytotoxic agent formulated into a prodrug form having substrate specificity for microvessel phosphatases, so that microvessels are destroyed preferentially over other normal tissues, because the less cytotoxic prodrug form is converted to the highly cytotoxic dephosphorylated form. Examples of preferred cytotoxic agents for vascular targeting are tubulin binding agents, because they can be transformed from water insolubility to water solubility, tubulin binding agents to non-tubulin binding agents, and cytotoxicity to non-cytotoxicity by phosphate prodrug formulation (Anti-Cancer Drug Design 13: 183–191, 1998).

Examples of the molecular diversity for targeting microvessel cellular toxicity by formation of phosphate prodrugs are presented in FIGS. 1A–1C, and they were selected from the known tubulin binding agents already previously listed such as the combretastatins, taxanes, vinblastine (vinca alkaloids), colchicinoids, dolastatins, podophyllotoxins, steganacins, amphethiniles, flavanoids, rhizoxins, curacins A, epothilones A and B, welwistatins, phenstatins, 2-strylquinazolin-4(3H)-ones, stilbenes, 2-aryl-1,8-naphthyridin-4(1H)-ones, 5,6-dihydroindolo(2,1-a) isoquinolines, 2,3-benzo(b)thiophenes, 2,3-substituted benzo(b)furans and 2,3-substituted indoles. The compounds listed in FIGS. 1A–1C satisfy the structural requirements of having either aromatic hydroxyl or amino groups present capable of chemical reaction to produce a phosphate salt, and the further conversion of a cytotoxic agent into a non-cytotoxic phosphate prodrug construct. Other criteria necessary for targeting vascular toxicity are:

1. Tubulin binding agents or other cytotoxic agents (e.g. pancratistatin has not been reported to bind to tubulin polymers) must induce similar levels of toxicity to both human microvessel cells and other normal human cells such as fibroblasts when in the cytotoxic (tubulin binding) form, or, alternatively, the tubulin binding form must be much less inherently cytotoxic to normal cells than to microvessel cells. If this were not the case and fibroblasts (i.e. normal cells) were much more sensitive than microvessels to the cytotoxic form, then when in the non-cytotoxic prodrug form, even though fibroblasts had much less phosphatase to activate the cytotoxic form, much less would in turn be needed to induce cytotoxicity in fibroblasts. The net result would be that prodrugs could still be more toxic to microvessels instead of normal cells, because of their enhanced alkaline phosphatase activity producing the cytotoxic form.
2. The tubulin binding or cytotoxic forms of potential phosphate prodrugs must not be cytotoxic in the prodrug form, which in turn needs to be converted into the cytotoxic form within 1–3 hours, preferably within 1–2 hours. Tubulin binding agents clear from peripheral circulation within a few hours. So in order to be effective in targeting vascular destruction in vivo, the phosphate prodrug constructs must be converted to the cytotoxic forms within 1–3 hours by phosphatase in the microvessels in order to elicit a preferential toxicity of the cells. Hence, the kinetics of binding to tubulin must be nearly complete within 1–3 hours.

Although high levels of alkaline phosphatase are useful for targeting vascular destruction of tubulin binding agents, this invention also embraces, in a broader sense, that any enzyme or protein specifically amplified in microvessels, and that is capable of converting metabolically a nontoxic prodrug into a cytotoxic drug, would be equally useful in targeting vascular destruction.

Compositions in accordance with the invention having use in targeting vascular destruction are illustratively exemplified, without limitation, by compounds embraced within the class of compounds having the general formula 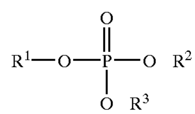 or 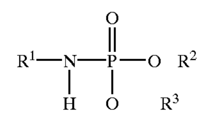 wherein $R^1$ is defined by the formula $R^1$—$R^a$ representing a compound that contains at least one group (designated $R^a$) which is a phenolic hydroxyl group, or an aromatic amino group, or any other appropriate hydroxyl or amino group, that can form $R^2$–$R^3$ phosphate metal or amine salts or phosphate esters that serve as substrates for non-specific vascular endothelial phosphatases, and are thereby converted from a relatively non-cytotoxic phosphate form to a cytotoxic hydroxyl or amino form.

Thus, in illustrative embodiments, $R^1$ is defined by the formula R—$R^a$ representing a compound that contains at least one phenolic hydroxyl group (designated $R^a$) that can form a sodium phosphate or other appropriate salt (e.g., $R^2$, $R^3$ may be Li, Na, K, Ca, Cs, Mg, Mn, Zn, piperazine, nicotinamide and other examples as found in International (PCT) patent application No. 99/US/5368, the entire disclosure of which is incorporated herein by this reference) that serves as a substrate for non-specific vascular endothelial phosphatases, and that is thereby converted from a relatively non-cytotoxic phosphate form to the cytotoxic phenolic hydroxyl form.

The invention particularly embraces discoveries made in ascertaining the heretofore unknown explanation for the observed apparent selective targeting of proliferating endothelial cells by combretastatin A4 disodium phosphate, and in recognizing the applicability of those discoveries to drugs other than combretastatin A4 and to the treatment of non-malignant as well as malignant disorders involving vascular proliferation.

The pertinent studies respecting combretastatin A4 disodium phosphate will now be further described.

Chemicals

GMP manufactured combretastatin A4 disodium phosphate was purchased from OXiGENE, Inc. (Boston) and dissolved in physiological saline for addition to cell cultures. Alkaline phosphatase was purchased from Sigma (P-6774) as a buffered solution and was added to cell cultures directly.

Cell culture

Four commercially available human cell lines were grown in the indicated media below in 5% $CO_2$, 80% humidity and 37° C.:

Figure 1A:
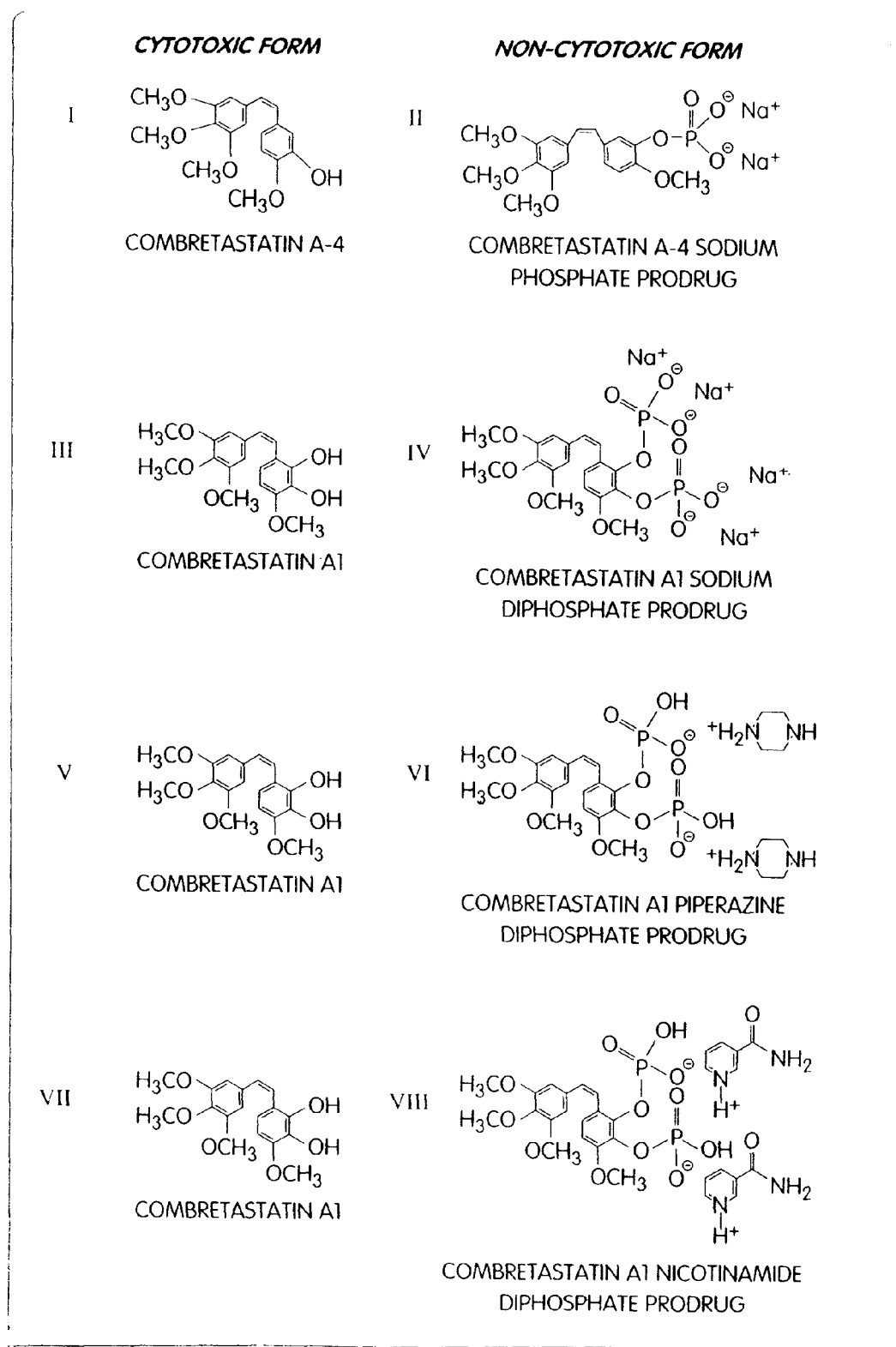

1. HL60 human leukemic cells, a pro-apoptotic cell line—cultured in RPMI 1640 fortified with 10% fetal calf serum.

2. K562 human leukemic cells, an apoptotic-resistant cell line—cultured in RPMI 1640 fortified with 10% fetal calf serum.

3. Human neonatal microvascular endothelial cells (HMVEC)—cultured in medium 131+microvascular growth supplement (MVGS)+attachment factor (AF)=500 ml+25 ml (AF is added 2–3 ml/T-25 flask; all reagents supplied by Cascade Biologics, Inc., Portland, Oreg.).

4. Human neonatal dermal fibroblasts (HDF)—cultured in medium 106+low serum growth supplement (LSGS)=500 ml+10 ml (Cascade Biologics, Inc.).

The cells used in all experiments were first subcultured up to 2–3 days at an initial density of $2 \times 10^5$ cells/ml prior to use in the vitro assays. This resulted in an exponential growth stage and the cell viability was >95% by trypan blue exclusion.

Cell Survival by Clonogenic Assay

This assay is based on a description reported by Schweitzer et al. (Expt. Haematol. 21: 573–578, 1993) with slight modifications. Briefly, HL60 and K562, HDF, HMVEC cells at concentrations of $4.2 \times 10^3$/ml were cultured in 96-well flat-bottomed microculture plates in a volume of 190 $\mu$l per well plus different concentrations of combretastatin A4 disodium phosphate or other tubulin binding agents and their prodrugs or units of alkaline phosphatase added in a 10 $\mu$l volume. After 5 days of incubation under the standard culture conditions stated above, colonies (>40 cells) were counted by an inverted light microscope or estimated by MTT assay. $IC_{50}$ values were obtained from the fitted curves of percentage of the control versus the drug concentrations.

Alkaline Phosphatase Metabolism of Combretastatin A4 Disodium Phosphate to the Highly Cytotoxic Combretastatin A4

There were three types of experiments designed to demonstrate the importance to convert A4 prodrug to A4 in order to target toxicity to vascular endothelial cells.

Experiment 1

HL60, K562, HDF, and HMVEC cells were either cultured in 96-well plates at the indicated concentrations (FIGS. 2A and 2B) for 5 days in the presence of A4 prodrug, or after 2 hours exposure the drug-containing media was removed, fresh media added, and the cells cultured for an additional 5 days. Clonogenic growth was recorded after 5 days incubation for all treatments.

Experiment 2

HMVEC and HDF were cultured in 96-well microtiter plates initially containing 800 cells/well. The cells were cultured for 1 hour in the presence of the indicated concentrations of A4 prodrug±1 unit of alkaline phosphatase. The medium was removed, the cells washed, and fresh medium added, and the cells were incubated for an additional 5 days. Clonogenic growth was then established by the MTT assay.

Experiment 3

HMVEC were cultured in 96-well microtiter plates initially containing 800 cells/well. The cells were cultured for 1 hour in the presence of the indicated concentrations of A4-prodrug±the indicated units of alkaline phosphatase. The medium was removed, the cells were washed in medium, and the cultures were further incubated in fresh medium for an additional 5 days. Clonogenic growth was then established by the MTT assay.

Figure 2A:
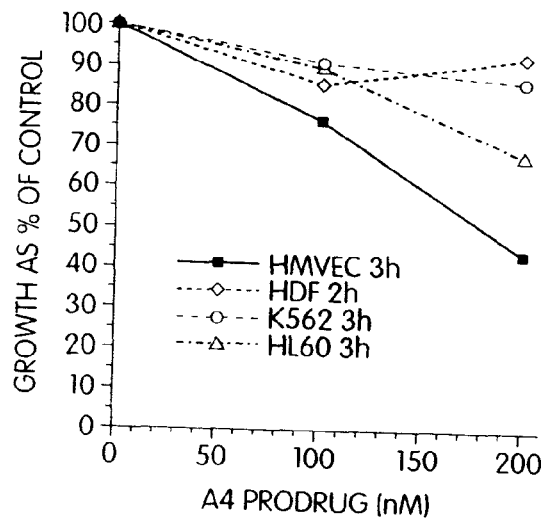
FIGS. 2A and 2B are graphs showing the effect of exposure time on combretastatin A4 prodrug cytotoxicity;
Figure 2B:
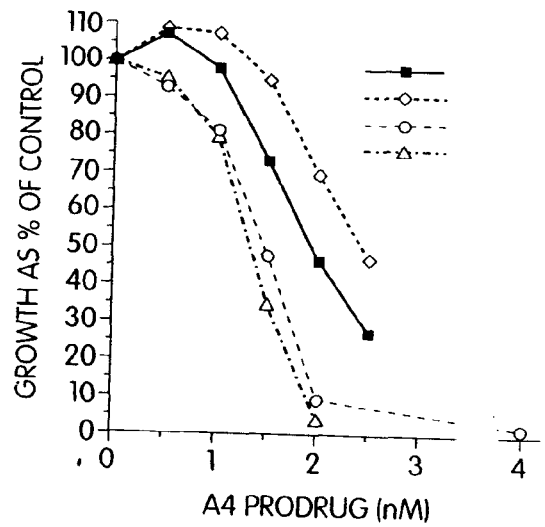

Referring to the drawings, FIGS. 2A and 2B are graphs showing the effect of exposure time on A4 prodrug cytotoxicity. HMVEC, HDF, HL60, and K562 cells were exposed for 2 hours (FIG. 2A) or 5 days (FIG. 2B) to combretastatin A4 disodium phosphate before clonogenic cytotoxicity was estimated at 5 days. Note that the $IC_{50}$ values were similar for all the cells after 5 days exposure being 1.5 to 2.5 nM whereas only HMVEC showed $IC_{50}$ cytotoxicity when exposure was limited to 2 hours.

Figure 3A:
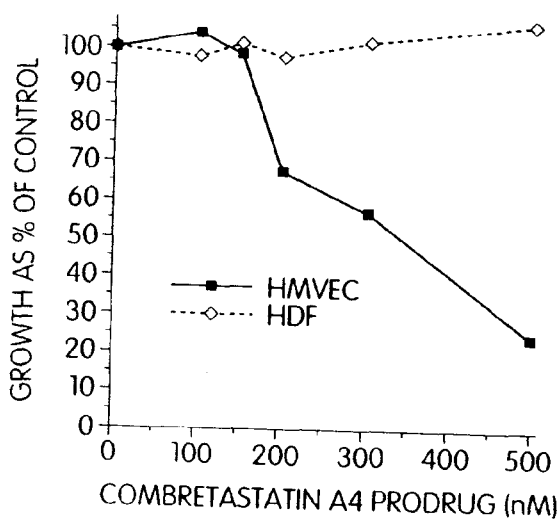
Figure 3B:
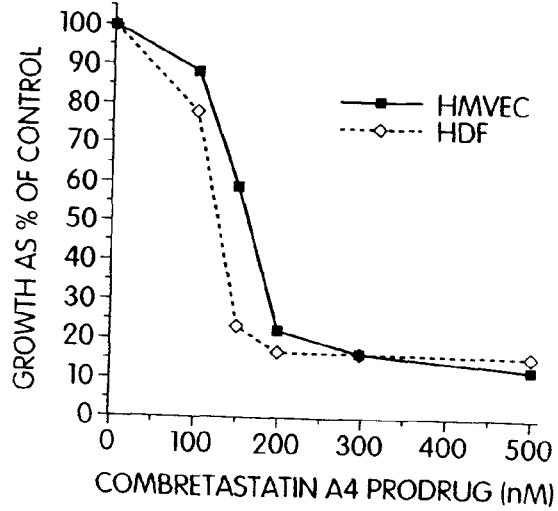

FIGS. 3A and 3B are graphs showing the effect of alkaline phosphatase on cultured HMVEC and HDF. Dose response cytotoxicity was estimated after 1 hour exposure to various concentrations of combretastatin A4 disodium phosphate in the presence or absence of 1 unit alkaline phosphatase. Note the lack of cytotoxicity of HDF without added alkaline phosphatase, but the cytotoxicity of A4 prodrug was the same for HMVEC and HDF when alkaline phosphatase was added.

Figure 4A:
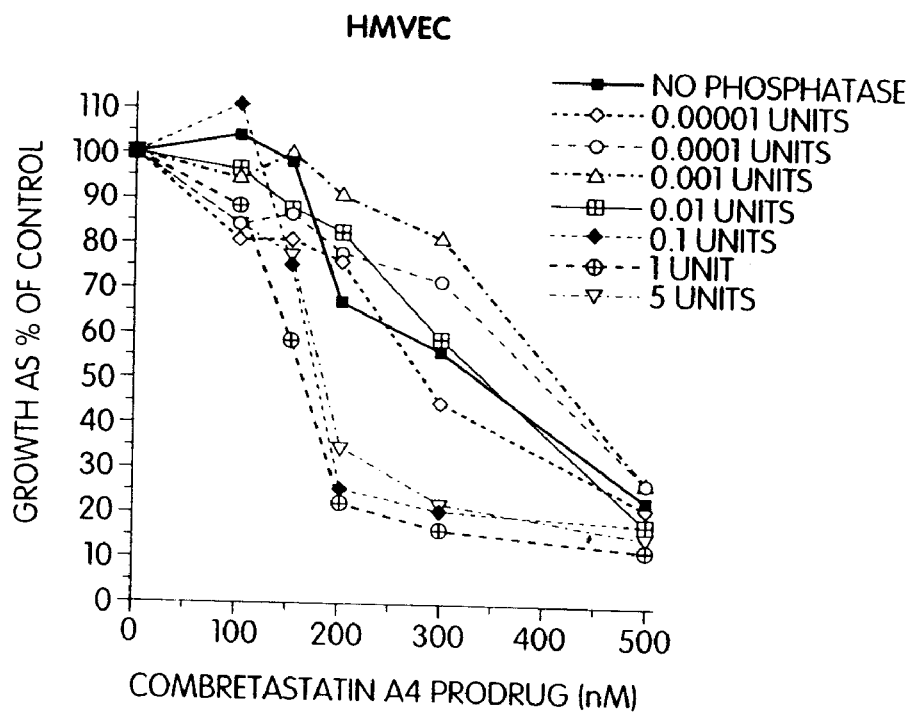
Figure 4B:
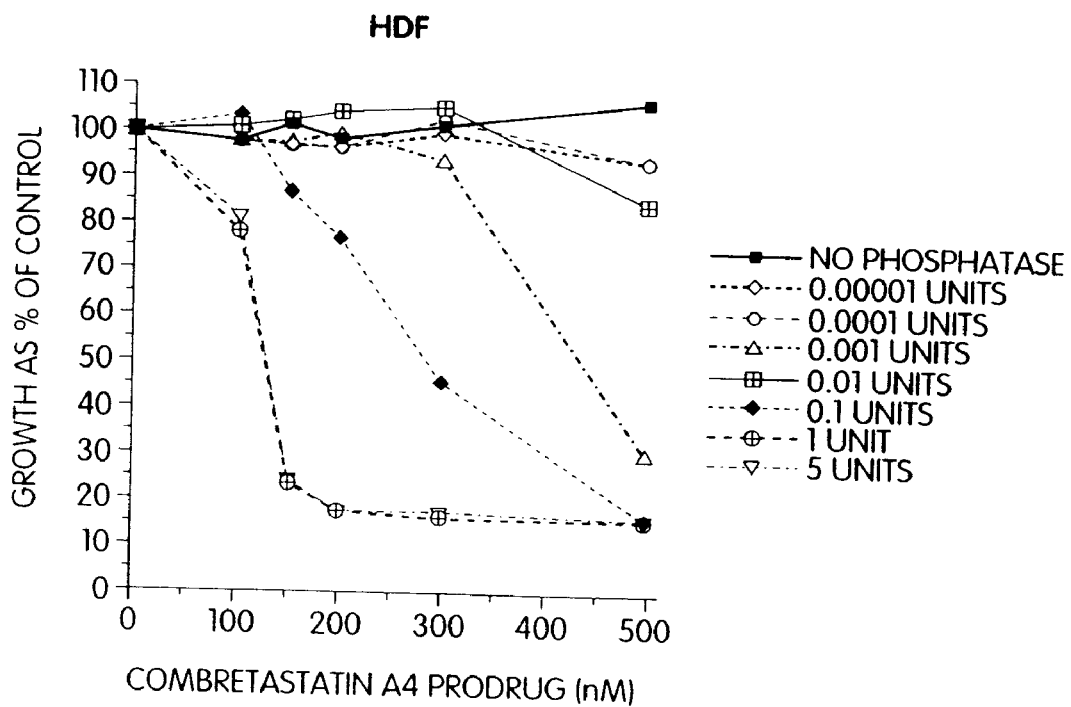

FIGS. 4A and 4B are graphs showing the dose response effect of added alkaline phosphatase on the cytotoxicity of HMVEC and HDF to A4 prodrug. HMVEC and HDF were cultured for 1 hour in the presence of the indicated concentrations of added combretastatin A4 disodium phosphate+ the indicated units of added alkaline phosphatase. The data clearly showed added dependence of the alkaline phosphatase on the cytotoxicity especially at the higher A4 prodrug concentrations.

EXAMPLE 1

Example 1 discloses the importance of time of exposure to the preferential cytotoxicity of vascular endothelial cells to tubulin binding agents such as combretastatin A4 prodrug. If the clonogenic assay is set up to treat HMVEC, HDF, K562 and HL60 cells for 5 days in the presence of increasing concentrations of combretastatin A4 disodium phosphate (prodrug), all the cell lines had similar $IC_{50}$ values of about 1.5 to 2.5 nM (FIG. 2B). These data teach that there is no inherent difference in the toxicity of the human cell lines regardless of their origin, if the exposure time is long enough. However, A4 prodrug, as well as other tubulin binding drugs, clear from peripheral circulation in vivo within a few hours, and under these conditions A4 prodrug showed a preferential toxicity to proliferating endothelial cells in tumors, whereas other tubulin binding agents have not been shown to possess this property (Cancer Res. 57(10):1829–1834, 1997). Hence, we have limited the exposure of the various cell lines to A4 prodrug for 2–3 hours, removed the A4-containing medium and replaced it with fresh medium, and continued culturing for an additional 5 days. These conditions showed that HMVEC were quite sensitive to A4 prodrug-induced cytotoxicity compared to the HDF, K562 and HL60 cells (FIG. 2A). These data teach that (i) an in vitro cell model can be used to demonstrate selective induction of toxicity to vascular endothelial cells by tubulin binding agents such as A4 prodrug, (ii) this only occurs under in vitro conditions that mimic in vivo pharmacokinetic-regulated limitations of exposure, and (iii) either tubulin binding parameters regulating cytotoxicity or metabolic differences or both are responsible for the selective toxicity of A4 prodrug to vascular endothelial cells.

EXAMPLE 2

The combretastatins are a family of naturally occurring tubulin binding agents comprising an A-,B-,C- and D-series of structures (U.S. Pat. Nos. 4,940,726; 4,996,237; 5,409, 953; and 5,569,786). Example 2 compares the 1C50 values of the clonogenic toxicity induced by a selection of these compounds in in vitro cultures of HDF, HMVEC and HL-60.

The compounds were added to microcultures in DMSO (i.e <0.5%) and toxicity was evaluated by MTT assay after 5–7 days in culture. The data in Table 1 show that the combretastatin analogs varied considerably in their overall clonogenic toxicity between the various analogs as well as between the different human cell types being evaluated. A4 had the most toxic mechanism of binding tubulin in all the cell types tested, and it showed no preference for clonogenic toxicity between the cell types. However, the cytotoxicity of the other combretastatins generally could be ranked according to the clonogenic toxicity of greatest to least toxic as:

HL-60>HDF>HMVEC.

These data establish the prerequisite for tubulin binding drugs to have a property whereby toxicity to normal cells is not much greater than that to HMVEC, if phosphate prodrugs are to be used in vascular targeting of antimitotic toxicity.

TABLE 1

| Combretastatin | IC$_{50}$ clonogenic toxicity values in nM | | |
|---|---|---|---|
| | HDF | HMVEC | HL-60 |
| A4 | 1–2 | 1–2 | 1–2 |
| A3 | 8–10 | >12 | 5 |
| A2 | 25–35 | 30–40 | 15 |
| A1 | 20 | 500 | n.d. |
| B1 | 200–300 | 200–300 | 500 |
| B2 | 1100 | 800–1000 | 125 |
| K-228 | 40–90 | 90–120 | 90 |
| K-332 | 800–900 | >1000 | 500 |

Combretastatins were kindly supplied by Professor G. R. Pettit of Arizona State University. HDF = human diploid fibroblasts; HVMEC = human microvessel endothelial cells; HL-60 = human myeloid leukemic cells

EXAMPLE 3

Figure 5:
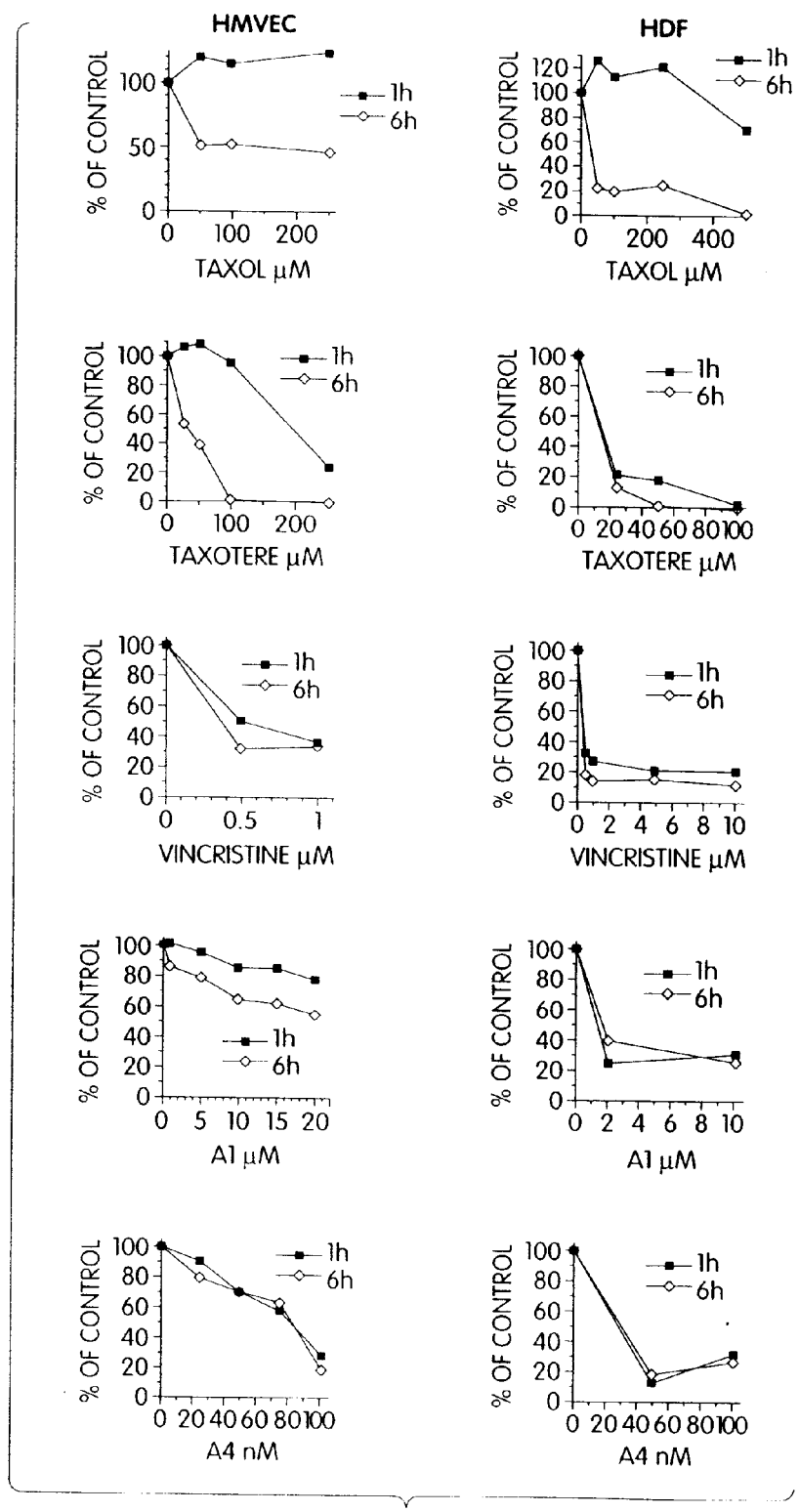

The effect of exposure time on the clonogenic toxicity induced by a variety of tubulin binding drugs is presented in FIG. 5. Taxol, taxotere, vincristine, and combretastatins A1 and A4 were added to microcultures of HMVEC and HDF for 1 and 6 hours, washed with saline and incubation continued in complete medium for 3 more days before estimating clonogenic toxicity by MTT assay. The data in this example show that the kinetics of binding of various tubulin binding drugs influences their cytotoxicity under conditions that are similar to in vivo exposure (i.e. 1 hour). For example, taxol, taxotere and Combretastatin A1 did not induce maximum toxicity to HMVEC after 1 hour exposure but required 6 hours, and in addition, the degree of kinetic-regulated cytotoxic responses were also different in HDF compared to HMVEC.

Hence, in order to target microvessel toxicity in humans the tubulin binding cytotoxic mechanism needs to be completed within a 1–3 hour period after treatment in a manner that permits the toxicity to HMVEC to be comparable to HDF or other normal cells. When this is the case then phosphate prodrugs are able to target microvessel toxicity because they have elevated alkaline phosphatase compared to normal cells to transform the prodrug into its cytotoxic form.

EXAMPLE 4

Both stress injury and the presence of invasive tumor cells can induce microvessels to produce up to 50-fold increased levels of alkaline phosphatase (J. Invest. Dermatol. 109(4) :597–603, 1997; FEBS Lett. 350(1):99–103, 1994). Alkaline phosphatases present in cell membranes and circulation can hydrolyze organic phosphate-containing compounds separating or freeing the phosphate salt portion (e.g. calcium phosphate) from the organic molecule portion. The physiological need of microvessels to repair damage to themselves by elevating alkaline phosphatases is a part of normal wound healing process leading to an increased deposition of calcium deposits in the injured area. A consequence of this metabolic specificity may be that cytotoxic tubulin binding agents modified into a phosphate salt (e.g. A4 prodrug) may also be a substrate for alkaline phosphatase. This process then could in turn lead to an increased cytotoxic sensitivity of microvessels to tubulin binding drugs, that do not bind tubulin in a phosphorylated form and are not cytotoxic to the dephosphorylated form which does bind tubulin and is cytotoxic. This example shows that indeed this is the case. HDF and HMVEC exposed to in vitro culture for 2 hours to increasing concentrations of A4 prodrug in the presence or absence of 1 unit of added alkaline phosphatase, demonstrate a high degree of selective cytotoxicity to HMVEC without added alkaline phosphatase, but HDF become identically cytotoxic as HMVEC to A4 prodrug in the presence of added alkaline phosphatase (FIGS. 3A and 3B). It was concluded that targeting vascular destruction was directly dependent on the presence of high levels of alkaline phosphatase in HMVEC, and the lack of it in other normal and tumor cells such as HDF. Hence, this example teaches a method for targeting preferential destruction of microvessels, whereby cytotoxic agents such as tubulin binding compounds, which when converted into a prodrug form by for example forming a phenolic hydroxy phosphate salt that cannot induce cytotoxicity, can be selectively metabolized by alkaline phosphatase, that is present in high amounts only in vascular endothelial cells, back into a cytotoxic form.

EXAMPLE 5

Example 5 further establishes and verifies the disclosure presented in Example 4. Here, the experimental design was designed to demonstrate the dose dependence of alkaline phosphatase on regulating cytotoxicity of A4 prodrug. The data clearly show how the amount of alkaline phosphatase determines the clonogenic cytotoxicity of combretastatin A4 disodium phosphate to both HMVEC and HDF (FIGS. 4A and 4B). The results teach that more alkaline phosphatase must be added before HDF can be killed by A4 prodrug, whereas HMVEC directly express clonogenic toxicity to A4 prodrug without or after addition of low levels of alkaline phosphatase, but at high added levels of alkaline phosphatase the toxicities become equal for both cell lines.

It is therefore demonstrated that in vivo targeting of tumor vascular destruction is directly dependent on alkaline phosphatase, and that this knowledge would be useful in designing agents and methods for the treatment of cancer and other, non-malignant, vascular proliferating disorders.

EXAMPLE 6

The compounds presented in Table 2 represent examples of how toxicity can be targeted to microvessel cells by converting the cytotoxic forms into phosphate prodrugs, which are in turn not cytotoxic until converted back into the cytotoxic form by cellular phosphatases such as alkaline phosphatase, which has ≧50-fold higher concentration in proliferating microvessel endothelial cells than other normal cells. In general, tubulin binding drugs cannot bind tubulin in the phosphate salt form, and so they represent a cytotoxic mechanism preferred as a cytotoxic mechanism for vascular targeting. All of the compounds were evaluated for toxicity after a one-hour exposure in microculture and assayed for cytotoxicity by MTT assay after an additional 5 days' incubation in culture. Under these conditions, the kinetics of tubulin binding were sufficiently rapid to cause toxicity in both normal proliferating HDF and HMVEC. The data reported in Table 2 establish that (i) phosphate prodrugs in general spare normal HDF from toxicity while not affecting the toxicity to HMVEC as shown by higher $IC_{50}$ values for the prodrugs in HDF but not HMVEC, (ii) if the cytotoxic agent is more toxic to HDF than to HMVEC, then even though the prodrug spares toxicity in HDF it cannot make up for the difference in inherent toxicities between HDF and HMVEC, (iii) not all metal or amine salts of phosphate prodrugs are equally effective since combretastatin A1 piperazine phosphate was only marginally effective at protecting HDF from cytotoxicity, and (iv) because pancratistatin is not known to bind tubulin, compounds having other cytotoxic mechanisms can also be targeted by the phosphatase mechanism. In summation, these data show that cytotoxic agents can target microvessel cellular destruction by phosphate prodrug construction, if there is protection for normal cells having little alkaline phosphatase to metabolize enough of the phosphate prodrug to its cytotoxic form within one hour of exposure (i.e., mimics in vivo conditions).

TABLE 2

Figure 1C:
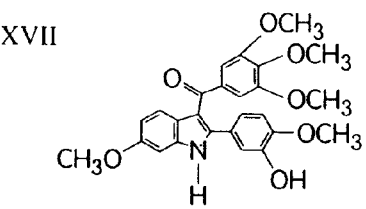
Figure 1C:
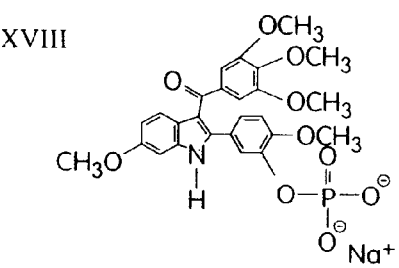
Figure 1C:
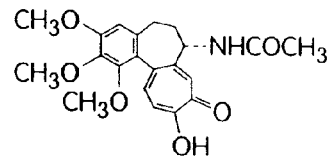
Figure 1C:
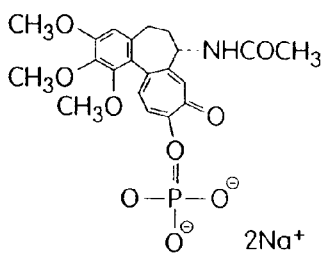
Figure 1C:
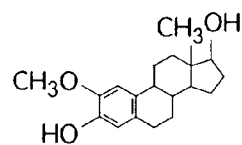
Figure 1C:
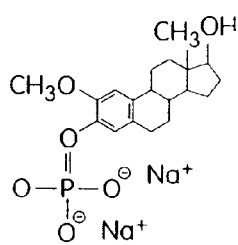

Evidence for targeting microvessel cellular toxicity by converting cytotoxic compounds into non-cytotoxic phosphate prodrugs (Note: "FIG. 1 No." in the left-hand column refers to the structure identification number in FIGS. 1A, 1B and 1C of the drawings. Compounds I to VIII were supplied by Professor G. R. Pettit of Arizona State University and compounds X to XVI by Dr. Kevin G. Pinney of Baylor University in Waco, TX)

| FIG. 1 No. | Cytotoxic form | Non-cytotoxic form (prodrug) | $IC_{50}$ values HMVEC | HDF |
|---|---|---|---|---|
| I | Combretastatin A4 | | 75–150 nM | 50 nM |
| II | | Combretastatin A4 $Na_2PO_4$ | 75–150 nM | >500 nM |
| III | Combretastatin A1 | | 10–15 μM | >0.5–1 μM |
| IV | | Combretastatin A1 $Na_2PO_4$ | 10–15 μM | 5–10 μM |
| V | Combretastatin A1 | | 10–15 μM | >0.5–1 μM |
| VI | | Combretastatin A1 Piperazine $PO_4$ | 10–15 μM | 1–2 μM |
| VII | Combretastatin A1 | | 10–15 μM | >0.5–1 μM |
| VIII | | Cornbretastatin A1 Nicotinamide $PO_4$ | 10–15 μM | >10 μM |
| X | | Amino Combretastatin A4 Phosphoroamidate | 8–10 μM | 15–20 μM |
| XI | Dihydronaphthalene | | 0.5–1 μM | 0.5–1 μM |
| XII | | Dihydronaphthalene Phosphoroamidate | 5–7 μM | >50 μM |
| XIII | Pancratistatin | | 20–25 μM | 20 μM |
| XIV | | Pancratistatin $Na_2PO_4$ | 20–25 μM | 60–80 μM |
| XV | Benzo(a)thiophene | | 5–10 μM | 5–10 μM |
| XVI | | Benzo(a)thiophene $Na_2PO_4$ | 8–10 μM | 30–40 μM |

EXAMPLE 7

To simulate pathogenic ocular angiogenesis, ocular neovascularization was induced by administration of lipid hydroperoxide (LHP) by intra-corneal injection at a dosage of 30 μg to rabbit eyes. Seven to 14 days later, ocular vessels formed in the injected eyes due to LHP insult. The subjects were divided into two groups; those of one group were given combretastatin A4 disodium phosphate by intravenous administration at a dosage of 40 mg/kg once a day for five days, while a vehicle without combretastatin A4 disodium phosphate was administered to the other group by i.v. administration as a dosage of water for the same time period. The eyes of both groups were examined seven days later. A reduction of vessels of 40% or more was observed in the group treated with combretastatin A4 disodium phosphate, but not in the other group.

It is to be understood that the invention is not limited to the features and embodiments hereinabove specifically set forth, but may be carried out in other ways without departure from its spirit.

What is claimed is:

1. A method of treating a warm-blooded animal having a vascular proliferative disorder, comprising administering, to the animal, an amount of a prodrug of a tubulin binding agent, other than combretastatin A4 disodium phosphate, effective to achieve targeted vascular destruction at a locality of proliferating vasculature, wherein the prodrug is substantially noncytotoxic but is convertible to a substantially cytotoxic drug by action of an endothelial enzyme.

2. A method according to claim 1, wherein the prodrug is phosphate within the class of compounds having the general formula:

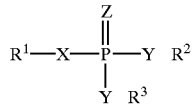

wherein:
X is O, NH or S;
Y is O, NH, S, O$^-$, NH$^-$, or S$^-$;
Z is O or S;
each of R$^2$ and R$^3$ is an alkyl group, H, a mono- or divalent cationic salt, or an ammonium cationic salt, and R$^2$ and R$^3$ may be the same or different; and
R$^1$ is defined by the formula R$^1$—R$^a$ representing a compound that is a tubulin binder and contains at least one group (designated R$^a$) which is a group, containing X, that can form a phosphate or other salt that serves as a substrate for non-specific vascular endothelial phosphatases, and is thereby converted from a relatively non-cytotoxic phosphate from to a cytotoxic R$^1$—R$^a$ form.

3. A method according to claim 2, wherein the tubulin binder may be a compound selected from the group consisting of combretastatins, taxanes, vinca alkaloids, colchicinoids, dolastatins, podophyllotoxins, steganacins, amphethiniles, flavanoids, rhizoxins, curacins A, epothilones A and B, welwistatins, phenstatins, 2-strylquinazolin-4(3H)-ones, stilbenes, 2-aryl-1,8-naphthyridin-4(1H)-ones, 5,6-dihydroindolo(2,1-a) isoquinolines, 2,3-benzo(b)thiophenes, 2,3-substituted benzo(b)furans, 2,3-substituted indoles and 2-methoxy estradiol.

4. A method according to claim 1, wherein the animal has microvessel cells at the locality of vascular proliferation, wherein the animal also has other cells which are nonmalignant, and wherein the substantially cytotoxic drug is not substantially more toxic to said nonmalignant other cells than to said microvessel cells.

5. A method according to claim 4, wherein the prodrug is converted to the substantially cytotoxic drug by the action of the endothelial enzyme within a period of not more than about three hours.

6. A method according to claim 1, wherein the prodrug is converted to the substantially cytotoxic drug by the action of the endothelial enzyme within a period of not more than about three hours.

7. A method of treating a warm-blooded animal having a nonmalignant vascular proliferative disorder, comprising administering, to the animal, an amount of a prodrug of a tubulin binding agent effective to achieve targeted vascular destruction at a locality of proliferating vasculature, wherein the prodrug is substantially noncytotoxic but is convertible to a substantially cytotoxic drug by action of an endothelial enzyme.

8. A method according to claim 7, wherein the prodrug is phosphate within the class of compounds having the general formula:

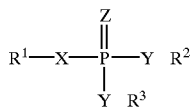

wherein:
X is O, NH or S;
Y is O, NH, S, O⁻, NH⁻, or S⁻;
Z is O or S;
each of $R^2$ and $R^3$ is an alkyl group, H, a mono- or divalent cationic salt, or an ammonium cationic salt, and $R^2$ and $R^3$ may be the same or different; and
$R^1$ is defined by the formula $R^1$—$R^a$ representing a compound that is a tubulin binder and contains at least one group (designated $R^a$) which is a group, containing X, that can form a phosphate or other salt that serves as a substrate for non-specific vascular endothelial phosphatases, and is thereby converted from a relatively non-cytotoxic phosphate from to a cytotoxic $R^1$—$R^a$ form.

9. A method according to claim 8, wherein the tubulin binder may be a compound selected from the group consisting of combretastatins, taxanes, vinca alkaloids, colchicinoids, dolastatins, podophyllotoxins, steganacins, amphethiniles, flavanoids, rhizoxins, curacins A, epothilones A and B, welwistatins, phenstatins, 2-strylquinazolin-4(3H)-ones, stilbenes, 2-aryl-1,8-naphthyridin-4(1H)-ones, 5,6-dihydroindolo(2,1-a) isoquinolines, 2,3-benzo(b)thiophenes, 2,3-substituted benzo(b)furans, 2,3-substituted indoles and 2-methoxy estradiol.

10. A method according to claim 7, wherein the animal has microvessel cells at the locality of vascular proliferation, wherein the animal also has other cells, and wherein the substantially cytotoxic drug is not substantially more toxic to said other cells than to said microvessel cells.

11. A method according to claim 10, wherein the prodrug is converted to the substantially cytotoxic drug by the action of the endothelial enzyme within a period of not more than about three hours.

12. A method according to claim 7, wherein the prodrug is converted to the substantially cytotoxic drug by the action of the endothelial enzyme within a period of not more than about three hours.

* * * * *